United States Patent [19]

Rutledge

[11] 4,101,561
[45] * Jul. 18, 1978

[54] OXIDATIVE COUPLING OF ALKYLPHENOLS CATALYZED BY METAL COMPLEXES OF IMINO ACID COMPOUNDS

[75] Inventor: Thomas F. Rutledge, Wilmington, Del.

[73] Assignee: ICI Americas Inc., Wilmington, Del.

[*] Notice: The portion of the term of this patent subsequent to Nov. 14, 1994, has been disclaimed.

[21] Appl. No.: 745,209

[22] Filed: Nov. 26, 1976

[51] Int. Cl.$^2$ .................. C07C 37/00; C07C 39/12; C07C 39/16; C07C 45/16; C07C 49/62; C07C 49/72

[52] U.S. Cl. .................. 260/396 N; 252/428; 252/430; 252/431 C; 260/613 R; 260/396 R; 568/730

[58] Field of Search ........... 260/396 N, 613 R, 619 B, 260/619 F, 620

[56] References Cited

U.S. PATENT DOCUMENTS

| | | | |
|---|---|---|---|
| 3,219,625 | 11/1965 | Blanchard et al. | 260/396 N |
| 3,219,626 | 11/1965 | Blanchard et al. | 260/396 N |
| 3,306,874 | 2/1967 | Hay | 260/396 N |
| 3,306,875 | 2/1967 | Hay | 260/396 N |

Primary Examiner—Vivian Garner
Attorney, Agent, or Firm—H. Jolyon Lammers

[57] ABSTRACT

Carbon-carbon coupled self-condensation products obtained by the oxidative coupling of alkylphenols are prepared by contacting an aqueous mixture of an alkyl phenol with oxygen in the presence of sufficient alkaline material to sustain a pH in the range of 8.5-9.5 during the oxidative coupling reaction and a catalyst system comprising certain imino acid chelates of $Cu^2$, $Ni^2$, $Co^2$, $Ce^3$, $Cr^3$, $Mn^2$ and $Fe^3$. The mixture may optionally contain a surfactant.

12 Claims, No Drawings

OXIDATIVE COUPLING OF ALKYLPHENOLS CATALYZED BY METAL COMPLEXES OF IMINO ACID COMPOUNDS

FIELD OF THE INVENTION

The present invention concerns generally an improved process for preparing self-condensation products, such as diphenoquinones, biphenols, dinaphthenoquinones and binaphthols from alkylphenols, alkoxyphenols and naphthols and to a catalyst composition for use in said process. More particularly, the invention concerns a method of preparing carbon-carbon coupled condensation products of alkylphenols, alkoxyphenols or 1-naphthols by contacting an aqueous mixture of the phenol or naphthol with oxygen or an oxygen-containing gas optionally in the presence of a surfactant and sufficient alkaline material to sustain a pH in the range of 8.5–9.5 during the oxidative coupling reaction and a catalyst system comprising an imino acid chelate of $Cu^2$, $Ni^2$, $Co^2$, $Ce^3$, $Cr^3$, $Mn^2$ or $Fe^3$ wherein the imino acid has the formula $$R-N[CH_2)_nCO_2H]_2$$

wherein $n$ is 1 or 2 and R is hydrogen, alkyl, hydroxy alkyl, oxaalkyl, cycloalkyl, aryl, pyridyl or —$(CH_2)_nCO_2H$ wherein $n$ is 1 or 2.

DESCRIPTION OF THE PRIOR ART

It is well known in the art that substituted phenols can be oxidized to yield self-condensation products, including diphenoquinones, biphenols and polyphenoxy ethers. The procedure employed in the preparation of these derivatives is generally referred to as the oxidative coupling of phenols.

The self-condensation products resulting from these oxidative coupling reactions can be catagorized as either the result of carbon-carbon coupling or carbon-oxygen coupling of said phenols. Diphenoquinones and biphenols are prepared by carbon-carbon coupling in accordance with the following general reactions depending upon the reactive sites available in the phenol employed.

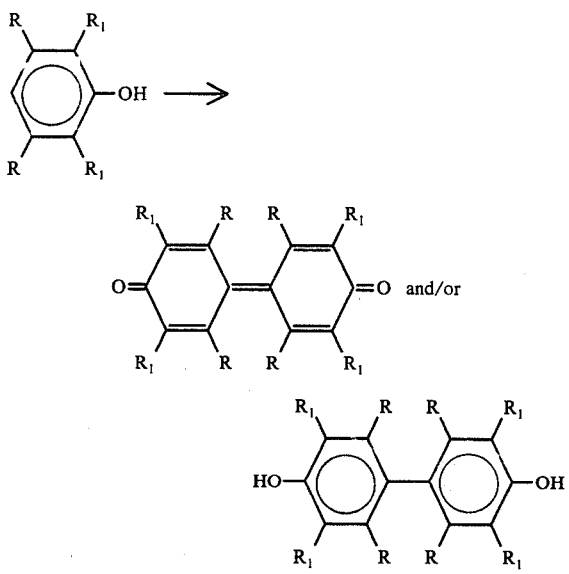

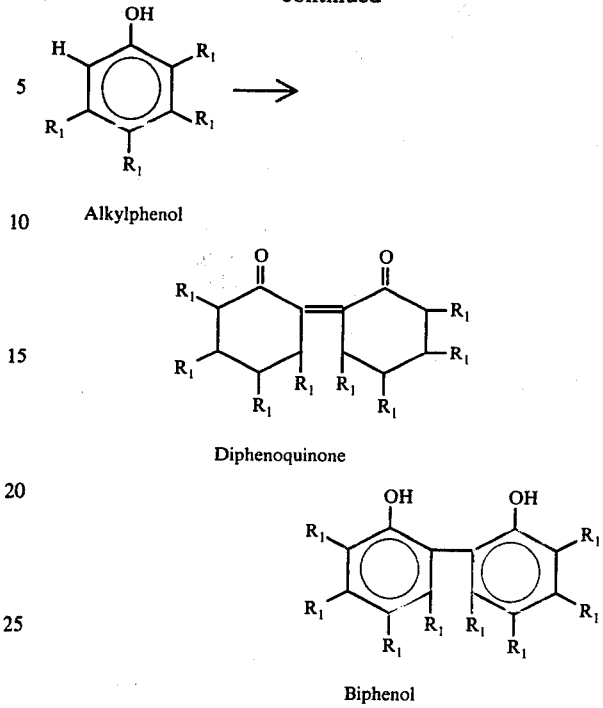

Alkylphenol

Diphenoquinone

Biphenol wherein R is hydrogen or $R_1$ and wherein $R_1$ is either alkyl, alkoxy, or another substitutent all of which are well known in the art.

Similar, polyphenoxy ethers are prepared by carbon-oxygen coupling in accordance with reactions such as the following general reaction:

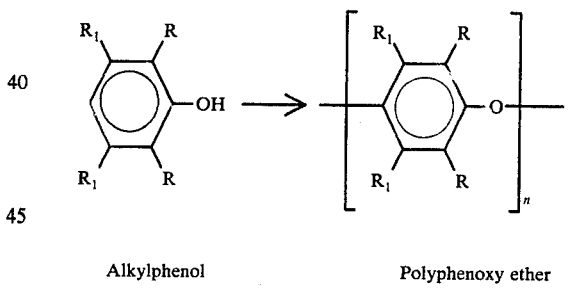

Alkylphenol       Polyphenoxy ether wherein R and $R_1$ are as defined above and $n$ is an integer.

A variety of materials, including metals and various salts and complexes thereof, have previously been disclosed as useful in promoting the oxidative coupling of alkylphenols. Thus, U.S. Pat. No. 2,785,188, discloses that copper powder may be utilized to prepare diphenoquinones from 2,6-dialkyl-4-halophenols. Similarly, various copper salts and combinations or complexes prepared from copper salts and a variety of nitrogen-containing compounds have been disclosed as useful in the preparation of both diphenoquinones and polyphenoxy ethers. These include, for example, cupric complexes of primary and secondary amines (U.S. Pat. No. 3,306,874); and cupric complexes of tertiary amines (U.S. Pat. Nos. 3,306,875 and 3,134,753).

The use of manganese amine chelates as oxidizing agents in oxidative coupling reactions is described in U.S. Pat. No. 3,825,521.

A variety of basic compounds have also been employed in oxidative coupling reactions. In many of these, such as those disclosed in U.S. Pat. Nos. 2,905,674, and 2,785,188, the function of the alkaline material was to react with an acidic component, such as HCl, liberated during the course of the reaction and, therefore, a stoichiometric amount of the base was used.

It should be noted that, previous methods of preparing coupled products from alkyl- or alkoxy-phenols have required the use of either organic solvents or stoichiometric amounts of organic oxidizing reagents. The present invention provides for a metal imino acid complex catalyst system useful in the preparation of carbon-carbon coupled phenols or naphthols in an aqueous reaction medium. Also, with most of the prior art systems the resulting product or products were determined by the particular catalyst employed and could not easily be controlled. The present invention provides for a system which can be readily modified to produce either the biphenol or diphenoquinone directly from the reaction mixture.

It has also been found that the type of product which is produced can be controlled by the amount of alkaline material and by the amount of catalyst employed in the catalyst system. By comparison, the prior art catalysts and processes employing said catalysts have a number of disadvantages which have restricted the utility of said catalysts and processes. These include (a) the requirement that the reaction be conducted in an organic solvent, (b) the fact that the primary product produced is often the polyphenoxy ether, and (c) the inability to form the biphenol, bisphenol and binaphthol derivative directly and in substantial quantities without requiring that this material be produced by a subsequent hydrogenation of the diphenoquinone, stilbenequinone or dinaphthenoquinone prepared in the oxidative coupling reaction. These disadvantages have been overcome by the use of the catalyst and process of the present invention as is described in detail hereinafter.

In accordance with the present invention, there is provided a method of preparing a condensation product of an "alkylphenol", an "alkoxyphenol" or a "1-naphthol", by an oxidative coupling reaction said method comprising contacting an aqueous mixture of the phenol or naphthol with oxygen or oxygen containing gas in the presence of sufficient amount of alkaline material to sustain pH in the range of about 8.5–9.5 during the oxidative coupling reaction and a catalyst system comprising an imino acid metal complex wherein the metal source is selected from the class of divalent copper, nickel, cobalt and manganese and trivalent cerium, chromium and iron; and wherein the imino acid has the formula:

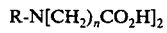

wherein $n$ is 1 or 2 and R is hydrogen, alkyl, oxaalkyl, hydroxy alkyl, cycloalkyl, aryl, pyridyl, or —$(CH_2)_n CO_2H$ wherein $n$ is 1 or 2. In a preferred embodiment the aqueous mixtures additionally contains a surfactant. The phenols or naphthols, metal complexes, and alkaline materials which may be utilized are critical to the present invention and are described in detail below.

Phenols/Naphthols

The phenols which may be employed in carrying out the present invention include both alkylphenols and alkoxyphenols. Specific phenols which may be utilized are described in detail below.

The alkylphenols which may be utilized are defined as any alkylphenol having at least two alkyl substituents, with the proviso that the phenols which have only two alkyl substituents must have the substituents in the ortho, ortho(2,6 in the formula below) or ortho, para (2,4 in the formula below) positions. These phenols are frequently referred to by the position of the alkyl substituent or substituents on the benzene ring as set forth in the following formula:

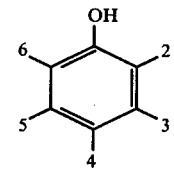

The process of the invention is applicable to any alkyl phenol having at least two alkyl substituents and steric properties such as to permit a coupling reaction. Thus if the para position is substituted with an alkyl group other than a methyl group, at least one ortho position must be unsubstituted. If one ortho and the para position are substituted, at least one of those substitutions must be a tertiary alkyl group. If both ortho positions are substituted, the para position must be either unsubstituted or substituted with a methyl group and no more than one meta position may be substituted with a tertiary alkyl group.

Thus, the alkylphenols will have one of the following formulas:

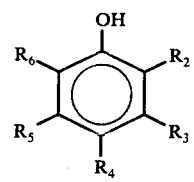

wherein $R_2$ and $R_6$ are alkyl and $R_3$, and $R_5$ are hydrogen or alkyl, and $R_4$ is hydrogen or methyl with the proviso that $R_3$ and $R_5$ cannot both be tertiary alkyl.

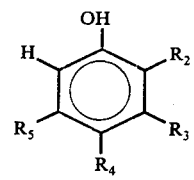

wherein $R_2$ and $R_4$ are alkyl provided that at least one of said alkyl groups is a tertiary alkyl and $R_3$ and $R_5$ are hydrogen or alkyl.

As used herein, the term alkyl refers to any monovalent radical derived from a saturated aliphatic hydrocarbon by removal of one hydrogen atom therefrom. The term includes both straight chain and branched chain materials containing from 1 to about 12 carbon atoms. Preferred results are achieved with alkylphenols wherein the alkyl substituent contains from 1 to about 5 carbon atoms.

The alkyl substituents are referred to herein as primary, secondary or tertiary alkyl depending upon the greatest number of carbon atoms attached to any single carbon atom in the chain.

Condensation products of any alkylphenol coming within the above-mentioned definition may be prepared in accordance with the present invention. As is apparent from that definition, the alkylphenols include dialkylphenols, trialkylphenols, and tetraalkylphenols. Specifically, the phenols which may be utilized include the following:

Ortho, para-substituted phenols including 2,4-dialkylphenols, 2,3,4-trialkylphenols, 2,4,5-trialkylphenols, and 2,3,4,5-tetraalkylphenols wherein the alkyl groups are either methyl or a primary, secondary, or tertiary alkyl provided that at least one of the alkyl groups in either the 2 or the 4 position is a tertiary alkyl, and ortho, ortho-substituted phenols including 2,6-dialkylphenols, 2,3,6-trialkylphenols and 2,3,5,6-tetraalkylphenols wherein the alkyl groups are either methyl or a primary, secondary, or tertiary alkyl provided that in the case of 2,3,5,6-tetraalkylphenols at least one of the alkyl groups in either the 3 or the 5 position is either a primary or secondary alkyl.

Representative ortho, para-substituted phenols which may be used include, for example 2,4-ditertiary-butylphenol, 2-methyl-4-tertiary-butylphenol, 2,-tertiary-butyl-4-methylphenol, 2,4-ditertiary-amylphenol, 2,4-ditertiary-hexylphenol, 2-isopropyl-4-tertiary-butylphenol, 2-secondary-butyl-4-tertiary-butylphenol, 2-tertiary-butyl-3-ethyl-4-methylphenol, 2,5-dimethyl-4-tertiary-butylphenol, and 2-methyl-3-ethyl-4-tertiary-butylphenol.

Representative 2,6-dialkylphenols (ortho, ortho-substituted) include, for example 2,6-xylenol, 2-methyl-6-butylphenol, 2,6-diisobutylphenol, 2-octyl-6-methylphenol, 2-isobutyl-6-dodecylphenol, 2,6-ditertiary-butylphenol, 2,6-ditertiary-hexylphenol, 2-ethyl-6-methylphenol, 2-methyl-6-tertiary-butylphenol, 2,6-diisopropylphenol, 2,6-di-secondary-butylphenol, and 2-cyclohexyl-6-methylphenol.

Representative 2,3,6-trialkylphenols which may be utilized in accordance with the present invention include, for example, 2,3,6-trimethylphenol, 2,3,6-triethylphenol, 2,6-dimethyl-3-ethylphenol, 2,3-diethyl-6-tertiary-butylphenol, and 2,6-ditertiarybutyl-3-methylphenol.

Representative 2,3,5,6-tetraalkylphenols which may be utilized in accordance with the present invention include, for example, 2,3,5,6-tetramethylphenol, 2,3,5,-trimethyl-6-tertiary-butylphenol, 2,6-ditertiary-butyl-3,5-dimethylphenol, 2,3,6-trimethyl-5-tertiary-butylphenol, 2,3-dimethyl-5,6-diethylphenol, and 2-methyl-3-ethyl-5-isopropyl-6-butylphenol.

When an ortho, para substituted alkylphenol is employed the coupling reaction proceeds in accordance with the following reaction resulting in the o, o'-coupled product.

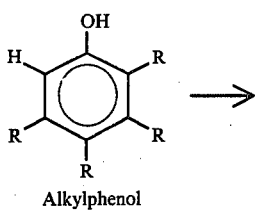
Alkylphenol

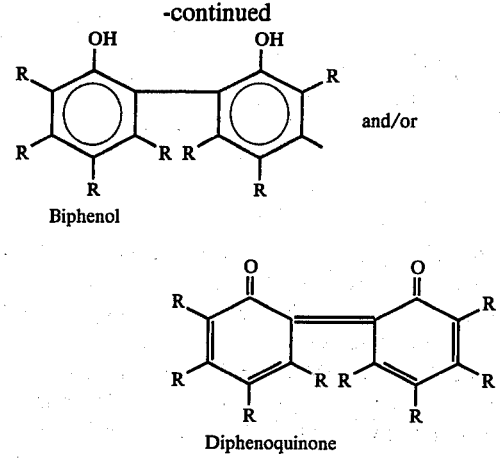
Biphenol and/or

Diphenoquinone

In this reaction each R represents hydrogen or an alkyl group as defined above depending upon whether di-, tri-, or tetra-substituted alkylphenol is utilized.

Similarly, with the ortho, ortho-substituted alkylphenols, the reaction results in the p,p'-coupled product in accordance with the following reaction wherein R is hydrogen or alkyl depending upon which of the above-mentioned alkylphenols is used as the starting material.

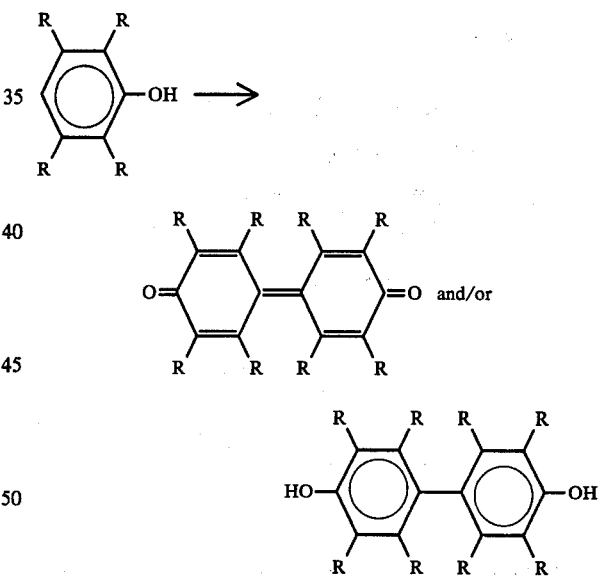

It has also been found that alkoxyphenols may be oxidatively coupled in accordance with the present invention. These include among others 2,6-disubstituted phenols wherein at least one of the substituents is an alkoxy group containing up to about six carbon atoms such as methoxy, ethoxy, propoxy, butoxy and pentoxy. In addition to the 2,6-dialkoxyphenols, 2-alkyl-6-alkoxyphenols, wherein the alkyl groups are as defined above for the alkylphenols, may be utilized. As used herein the term alkoxyphenols is intended to include both types of compounds. These compounds may be represented by the following general formulas:

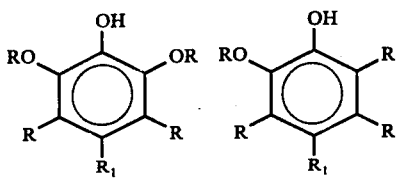
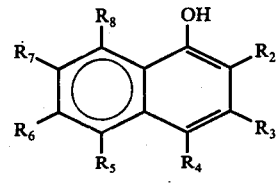

wherein each R is any alkyl group as defined above for the alkylphenols or OR and $R_1$ is either hydrogen or methyl, provided that the substituents adjacent to $R_1$ cannot both be tertiary alkyl or tertiary alkoxy. Representative alkoxyphenols which may be utilized include, for example, 2,6-dimethoxyphenol, 2,6-diethoxyphenol, 2,6-dibutoxyphenol, 2-methoxy-6-pentoxyphenyl, 2-methyl-6-methoxyphenol and 2-ethyl-6-propoxyphenol, 2-methoxy-3-ethoxy-6 methylphenol.

When these phenols are utilized the reaction proceeds in accordance with the following representative reaction resulting in the p,p'-coupled material.

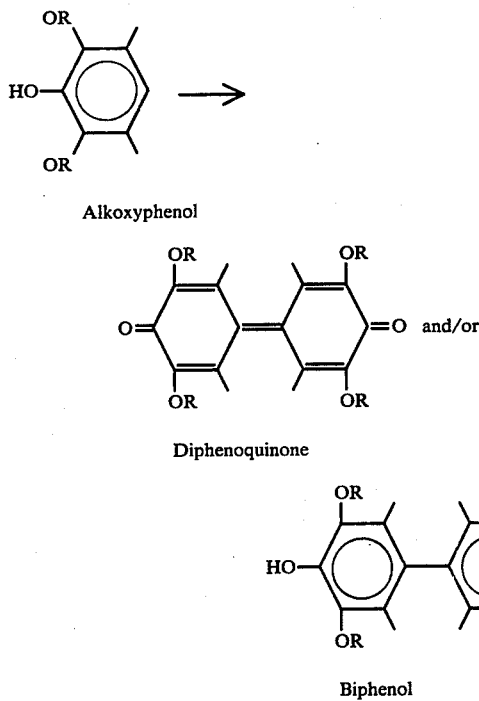

Mixtures of 2 different phenols may also be utilized. When this is done, there generally results a mixture of three different materials. Two of these are the products of the oxidative coupling of one molecule of one of the phenols with a second molecule of the same phenol. The third product is that resulting from the oxidative coupling of one molecule of the first phenol with one molecule of the second phenol. The products may be separated prior to use, as is well understood in the art.

Moreover, 1-naphthol and substituted 1-naphthols having at least 1 unsubstituted position ortho or para to the hydroxyl group may also be employed. The naphthols which may be coupled in accordance with the present invention are represented by the following general formula:

wherein $R_2$, $R_3$ and $R_4$ are hydrogen, alkyl containing from 1 to 5 carbon atoms, or alkoxy containing from 1 to 6 carbon atoms, provided that either or both $R_2$ or $R_4$ are hydrogen and $R_5$, $R_6$, $R_7$, and $R_8$ are hydrogen, alkyl containing from 1 to 5 carbon atoms or alkoxy containing from 1 to 6 carbon atoms provided that tertiary alkyl or tertiary alkoxy groups may not be attached to adjacent carbon atoms of the naphthalene molecule.

Representative naphthols which may be utilized include, for example, 1-naphthol, 2-methyl-1-naphthol, 2,3-dimethyl-1-naphthol, 4-ethyl-1-naphthol, and 2-methoxy-1-naphthol.

When a naphthol is employed, the coupling reaction takes place in accordance with the following general reactions depending upon the reactive positions — i.e., those either ortho or para to the hydroxy group — available. Thus, if $R_2$ is hydrogen and $R_4$ is alkyl or alkoxy

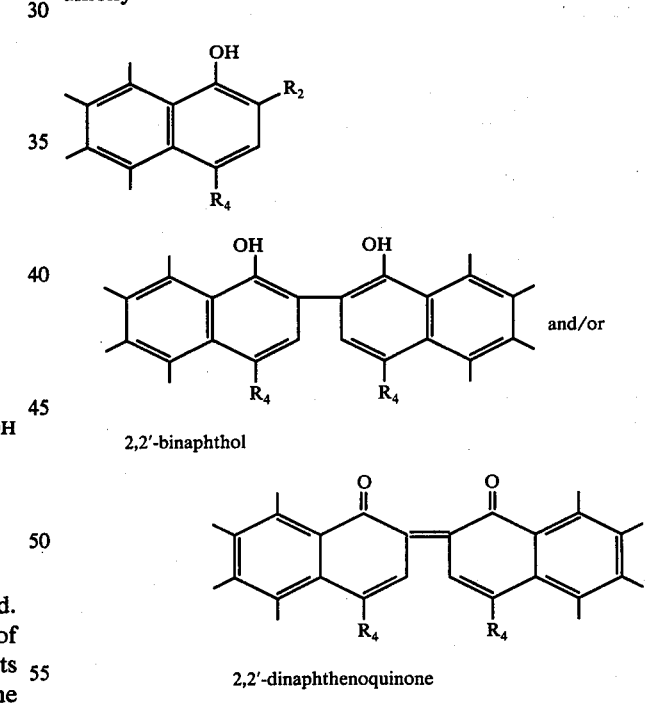

Similarly, if $R_4$ is hydrogen and $R_2$ is alkyl or alkoxy, the products are the 4,4'-binaphthol and the 4,4'-dinaphthenoquinone. When both $R_2$ and $R_4$ are hydrogen the products may be a mixture of the 2,2'-; 2,4'- and 4,4'-binaphthols and dinaphthenoquinones.

Finally, the catalyst system of this invention may also be employed to prepare coupled products of alkylphenols wherein all of the positions ortho and para to the hydroxy group are substituted and the substituent para to the hydroxy group is methyl. These alkylphenols may be represented by the following general formula:

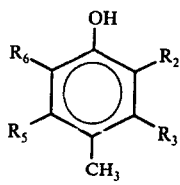

V wherein
R$_3$ is hydrogen, a primary, secondary or tertiary alkyl or an alkoxy group:
R$_5$ is a primary or secondary alkyl group containing from 1-5 carbon atoms and R$_2$ and R$_6$ are a primary, secondary or tertiary alkyl or an alkoxy group.

Representative compounds which may be employed include, for example, 2,4,6-trimethylphenol; 2,6-di-secondary-butyl-4-methylphenol; 2-methyl-6-t-butyl-4-methylphenol; and 2,3,4,6-tetramethylphenol.

When one of these alkylphenols is employed, the reaction proceeds in accordance with the following general reaction to produce the stilbenequinone or bisphenol derivative. These materials are useful in the same applications set forth above for the diphenoquinones, dinaphthenoquinones, biphenols and binaphthols.

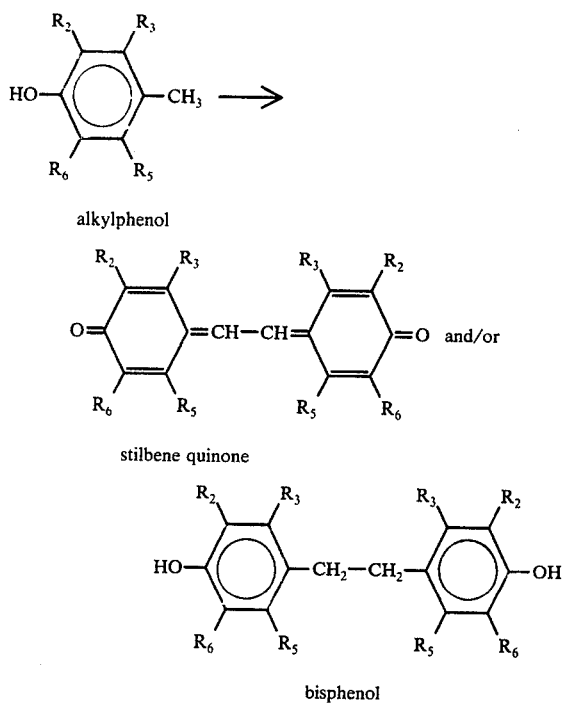

wherein the substituent values are those specified in formula V.

It should be specifically noted that the term "alkyl phenol" is hereby defined as only those alkyl phenols of formulas I, II and V and their isomers, the term "alkoxy phenol" is hereby defined as only those alkoxy phenols of formula III and their isomers and that the term "1-naphthol" is defined as only those 1-naphthols of formula IV and their isomers.

Metal Complex

One of the essential components of the catalyst system of the present invention is a metal imino acid complex. As mentioned hereinbefore the metal source for this complex may be divalent copper, nickel, cobalt or manganese or trivalent chromium, iron or cerium.

The imino acid compounds which may be complexed with the metal ion source useful in achieving the improved results of the present invention have the following structural formula:

R—N[(CH$_2$)$_n$CO$_2$H]$_2$ wherein R is hydrogen, hydroxy alkyl, oxaalkyl, cycloalkyl, aryl, pyridyl or —(CH$_2$)$_n$CO$_2$H and wherein n is 1 to 2. Useful imino acids encompassed by the above formula include:
HN(CH$_2$CO$_2$H)$_2$ — nitrilodiacetic acid
N(CH$_2$CO$_2$H)$_3$ — nitrilotriacetic acid
HOCH$_2$CH$_2$N(CH$_2$CO$_2$H)$_2$ — N-(2-hydroxyethyl)-iminodiacetic acid
N(CH$_2$CH$_2$CO$_2$H)$_3$ — nitrilotripropionic acid

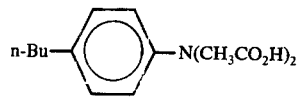

p-n-butylanilinediacetic acid

In accordance with the invention the imino acid is complexed with a source of certain metal ions. These ions may be derived from the corresponding metal salts and may include any of the following:
halides, such as chloride, bromide and iodide,
basic halo hydroxides such as for example represented by the formula CuX$_2$.Cu(OH)$_2$ or CoX$_2$.CO(OH)$_2$ wherein X is chlorine, fluorine, bromine, or iodine,
carboxylates, such as acetate, benzoate, and butyrate
nitrates
sulfates
alkyl sulfates wherein the alkyl group is either a straight or branched chain alkyl containing from 1 to about 20 carbon atoms including, for example, methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, and eicosyl,
aryl sulfonates wherein the aryl group contains at least one aromatic ring which may, if desired, have alkyl substituents such as those mentioned above, attached thereto including, for example, benzene, naphthalene, dodecyl benzene, and methyl naphthalene.
carbonates,
basic carbonate — i.e., CuCO$_3$.Cu(OH)$_2$,2CoCO$_3$.Co(OH)$_2$.H$_2$O
hydroxides,
chlorates — i.e., Cu(ClO$_3$)$_2$, These complexes may be prepared in any manner and the preparation thereof has not been found to be critical to the present invention. Similarly the ratio of imino acid to metal source has been found to be not narrowly critical. It should be noted that if the ratio of imino acid to metal source is less than one, less complex is formed. The following three methods have been employed but other methods which will be readily apparent to those skilled in the art from the description of the invention given herein, may also be utilized.

First, suitable amounts of the imino acid and a source of metal ions may be combined in a suitable medium such as water and reacted to form the complex. The complex is prepared by simply stirring the solution for a period of time. If desired, heat may be applied to accelerate formation of the complex.

Alternatively, the imino acid and the source of the metal ion may simply be combined and added to the reaction mixture wherein the complex of the imino acid is formed. When this is done, any basic compound required to neutralize acidic by-products of the complex forming reaction is also added directly to the reaction mixture.

Finally, the imino acid, the source of metal ion, and any required basic compound may be added separately to the reaction medium and the complex formed in situ. As mentioned above, the method by which the metal complex is prepared has not been found to be critical to the present invention. However, further improved conversion results have been achieved when the source of metal ion and the imino acid are combined prior to addition to the reaction medium.

It should be noted that the complex formed by combining the imino acid or salt thereof with a metal ion source is referred to herein as a metal imino acid complex despite the fact that the complex contains no free acid groups. The use of such terminology is well understood in the literature. See for example, Bailar's *Chemistry of Coordination Compounds*, Reinhold Publishing Company 1956.

The amount of metal complex employed has not been found to be narrowly critical to the process of the present invention. However, it is preferred to employ at least 0.02 mmol of the complex per 100 mmols of alkylphenol. If less than this amount is used, the reaction is slower and the yields are low. Similarly, the maximum amount of complex employed is not generally greater than 1 mmol of the complex per 100 mmols of alkylphenol. At amounts much in excess of this the cost of the catalyst results in a uneconomic system.

Although any of the above-mentioned metal complexes may be used, improved conversion results have been achieved with the cupric complexes of nitrilodiacetic acid.

As mentioned above, an advantage of the catalyst system and of the process of the present invention is that the reaction can be carried out in an aqueous medium instead of an organic solvent as has been used in prior art system. However, it has not been found to be critical to the present invention to employ a water soluble metal complex. Thus, materials which are insoluble in water as well as those which are soluble may be utilized.

Surfactant

The catalyst composition of the present invention may also include, as an optional component thereof, a surfactant. The presence of a surfactant moderately improves conversion results and additionally allows easier cleaning of large reactors. A variety of surfactants also known as dispersants, are well known in the art and, as used herein, the term surfactant is intended to refer to organic compounds that contain in the molecule both hydrophobic and hydrophilic groups.

Surfactants are often classified, based on the hydrophilic (water liking) group which they contain, as either anionic, cationic, nonionic, or amphorteric. Any such surfactants may be employed in the present invention.

Surfactants are discussed in detail in the *Encyclopedia of Chemical Technology*, Kirk-Othmer, Second Edition Vol. 19 at pages 508-589, and any of the surfactants described therein may be utilized in the present invention.

The amount of surfactant employed has not been found to be critical to the utility of the catalyst system in carrying out the improved process of the present invention. However, if the use of a surfactant is desirable such as for example to increase the amount of carbon-carbon coupled product, there should be included in the reaction mixture at least about 0.1 mmols of surfactant per 400 mmol of phenol or naphthol. Preferred conversion results are achieved when the amount of surfactant employed is equal to from about 0.1 to about 0.6 mmols of surfactant per 400 mmol of phenol or naphthol. Additional amounts of the surfactant may be employed; however, the use of greater amounts of surfactant has usually not been found to significantly increase the total yield of product and it is, therefore, not generally desirable to include additional material in the reaction mixture.

Alkaline Material

In accordance with the present invention, an alkaline material is also included in the catalyst composition to ensure that the pH during the reaction is maintained in the range of 8.5-9.5. It has been found that the use of an alkaline material to raise the pH in the present system increases the conversion to carbon-carbon coupled products and decreases the conversion to carbon-oxygen coupled products. The use of such a material to maintain the required pH also increases the rate of the oxidative coupling reaction and decreases the amount of the metal compound which must be utilized.

The alkaline material useful in achieving the pH of the reaction and the improved results of the present invention is selected from the group consisting of alkali metal hydroxides, alkali metal carbonates, and alkali metal bicarbonates. The alkaline material may be added either as a single compound or as a mixture of compounds. Representative materials which may be employed include, for example, sodium hydroxide, potassium hydroxide, lithium hydroxide, sodium carbonate, lithium carbonate, sodium bicarbonate, rubidium carbonate, rubidium hydroxide, cesium bicarbonate, and cesium hydroxide.

The amount of alkaline material employed has not been found to be narrowly critical to the present invention as long as the required pH is maintained. However, preferred results are achieved when the amount of said material is equal to at least about 20 millimols per 100 mols of phenol or naphthol. Smaller amounts of alkaline material will normally result in a reaction pH of less than 8.5 and will normally cause a low molar conversion of starting compound to final product. A preferred pH is from about 9. Increased amounts of alkaline material may also be utilized in carrying out the present invention. It has been found that, for a given set of reaction conditions, increasing the amount of alkaline material increases the total conversion to carbon-carbon coupled products and the relative amount of diphenoquinone, stilbenequinone, or dinaphthenoquinone as compared to the amount of biphenol, bisphenol or binaphthol. Thus, by varying the amount of alkaline material to vary the pH within the required pH range of 8.5-9.5, the type of product can be controlled.

Besides the selective production of carbon-carbon coupled products, an additional advantage of the catalyst system of the present invention is the ability to control the type of carbon-carbon coupled product produced. Thus, it is possible to prepare selectively either diphenoquinone or biphenol, stilbenequinone, or bisphenol, or dinaphthenoquinone or binaphthol, in accordance with the present invention. This result is achieved by controlling the amount of alkaline material included in the system. Generally, as the amount of alkaline material is increased, the percentage of quinone derivative produced also increases. pH values higher than those suggested resulted in significant levels of oligomer formation. (carbon-oxygen coupled products.)

Reaction Conditions

As mentioned above, an advantage of the catalyst system and process of the present invention is that it makes it possible for the oxidative coupling reaction to be carried out in an aqueous medium. The amount of water employed has not been found to be critical to the present invention and any amount of water which will permit the reaction mixture to be stirred during the course of the reaction may be employed. It should also be noted again that it is not essential that the various components be soluble in water and the term aqueous mixture as used herein is intended to include solutions, slurries, suspension and the like.

The components of the reaction mixture may be combined in any suitable manner. Thus, the phenol or naphthol, surfactant, metal complex, alkaline material and water may be combined in any order in a suitable reaction vessel. Alternatively, and in a preferred method, the phenol or naphthol and optionally the surfactant are combined in water in a suitable reaction vessel, the mixture is stirred rapidly, preferably by utilizing a stainless steel impeller turning at 3,000–10,000 RPM and an aqueous mixture of the metal salt compound is prepared to which the amine is added followed by an aqueous solution of the alkaline material. In modifications of this procedure the metal complex may be added prior to heating or the metal complex and alkaline material may be combined prior to addition to the reaction mixture.

The reaction mixture comprising phenol or naphthol, water, metal complex and alkaline material is contacted with a suitable oxidizing agent to convert the phenol or naphthol to the desired product. Oxidizing agents which may be employed in carrying out the present invention include oxygen either alone or as an oxygen-containing gas, such as air. The oxygen may be introduced into the reaction mixture either directly as oxygen gas or an an oxygen-generating material such as ozone, hydrogen peroxide, or an organic peroxide. The amount of oxygen utilized should be sufficient to obtain the desired conversion of the phenol or naphthol to the coupled product. To assure that sufficient oxygen is present, oxygen should be introduced into the reaction mixture continuously during the course of the reaction.

The reaction conditions — i.e., time and temperature — employed have not been found to be narrowly critical to the process of the present invention. Preferred results have been achieved when the reaction mixture is maintained at from about 80° to 90° C. during the course of the reaction. However, temperatures above and below this preferred range may be utilized. At lower temperatures the reaction rate is reduced and at temperatures below about 40° C. it is so slow as to result in an uneconomic system. When operating at atmospheric pressure, as is desirable in some commercial operations, the practical upper limit on the temperature is 100° C., the boiling point of the water.

If the reaction is conducted at increased oxygen pressure, the reaction time is decreased, the total yield of coupled product is usually increased, and the relative amount of quinone derivative is also usually increased.

The amount of time required for completion of the reaction depends on the temperature employed and other variables such as the pressure, concentration of phenol or naphthol and the amount of metal complex, surfactant if present, and alkaline material employed. However, it has been found that, when conducted at atmospheric pressure, the reaction is usually completed in 6 hours or less.

Although, as mentioned above, the process of the present invention results primarily in the production of carbon-carbon coupled products, there are also sometimes included in the solids removed from the reaction mixture the following: (a) unreacted phenol or naphthol, and (b) low molecular weight polyphenoxy ether. The polyphenoxy ether and phenol or naphthol may be removed by washing the solids with a solvent in which these materials are soluble, such as an aromatic hydrocarbon — e.g., toluene, benzene, or a halogenated solvent — e.g., methylene chloride. If it is desired to separate the materials from each other and from the solvent, this may be done by distillation.

If the reaction results in the mixture of biphenol and diphenoquinone, bisphenol and stilbene quinone, or binaphthol and dinaphthenoquinone, these materials may be separated by any method known in the art. An especially convenient way of separating the materials is to stir the solid product with a dilute aqueous solution of sodium hydroxide, which converts the biphenol, bisphenol or binaphthol to the sodium salt which is usually soluble in water. The insoluble diphenoquinone, stilbene quinone or dinaphthenoquinone may then be filtered off and the biphenol, bisphenol or binaphthol recovered by adding the aqueous solution of the sodium salt thereof to a dilute solution of a strong acid such as hydrochloric acid from which the biphenol, bisphenol or binaphthol precipitates, Alternatively, the entire product may be hydrogenated or chemically reduced and converted to only the biphenol, bisphenol or binaphthol.

The diphenoquinones and/or biphenols as well as the binaphthols, bisphenols and dinaphthenoquinones and stilbene quinones produced in accordance with the present invention are suitable for any of the uses of these materials which have heretofore been described in the art. Thus, the diphenoquinones and dinaphthenoquinones may be used as inhibitors of oxidation, peroxidation, polymerization and gum formation in gasolines, aldehydes, fatty oils, lubricating oils, ethers and similar compounds as mentioned in U.S. Pat. No. 2,905,674 issued to Filbey. The diphenoquinones may also be hydrogenated, employing conventional techniques, to yield the corresponding biphenol. The biphenols may be employed as stabilizers in gasoline and other petroleum products as described in U.S. Pat. No. 2,479,948 issued to Luten et al. They may also be utilized as intermediates in the manufacture of such useful products as sulfones, carbonates and epoxy resins. In order to describe the present invention so it may be more clearly understood the following examples are set forth. These examples are given primarily for the purpose of illustration and any enumeration of detail contained therein should not be interpreted as a limitation on the concept of the present invention.

EXAMPLE 1

Into a first flask there were added;

0.4 grams (2 mmols) of cupric acetate $Cu(OAc)_2 \cdot H_2O$,
0.40 grams (2 mmols) of disodium nitrilodiacetate,
25 grams of ion exchanged water.

Into a 500 ml creased Morton flask, fitted with a gas addition tube, a condenser, a thermometer, and a stirrer capable of operating at speeds in the range of from about 3,000 to about 10,000 rpm there were added; 0.1 grams of sodium lauryl sulfate, 200 grams of deionized water and 48.8 grams (400 mmols) of 2,6-xylenol.

To the resulting slurry which was stirred using a Labline cruciform stainless steel impeller turning at about 6,000 rpm there was added the stirred copper imino acid complex solution prepared above. The resulting mixture was stirred for 15 minutes and heated to 80° C. 1.82 gms of sodium hydroxide (as 45.5 ml of 1.0 N) solution was added during the course of the reaction to maintain the pH of the mixture at 9. The mixture was stirred under oxygen. The oxygen flow was rapid at the beginning to flush the system. After about ½ hour, oxygen flow was reduced and maintained at a level sufficient to cause slow bubbling in a bubbler attached to the top of the condenser. The temperature was controlled by a Therm-O-Watch temperature controller. The reaction mixture was stirred vigorously and maintained under oxygen for the prescribed reaction time of 6 hours.

Product Isolation

The reaction slurry was cooled to room temperature, acidified to pH3 with HCl, filtered to remove the water phase. A sample of the solid was removed, dissolved in acetone and analyzed by gas-liquid chromatography. The analysis indicated that 99+ weight percent of the 2,6-xylenol was converted.

The solid product was then washed with xylene to remove oligomer and dried at 60° C. overnight. 37.4 gm of product was obtained as a green solid which contained 44 weight percent diphenoquinone and 56 weight percent tetramethylbiphenol as determined by spectrophotometric analysis.

EXAMPLE 2

Into a first flask there were added:

0.4 grams (2 mmols) of cupric acetate $Cu(OAc)_2 \cdot H_2O$,
0.28 grams (1 mmol) of trisodium nitrilotriacetate,
25 grams of ion exchanged water.

Into a 500 ml creased Morton flask, fitted with a gas addition tube, a condenser, a thermometer, and a stirrer capable of operating at speeds in the range of from about 3,000 to about 10,000 rpm there were added; 0.1 grams of sodium lauryl sulfate, 200 grams of deionized water and 48.8 grams (400 mmols) of 2,6-xylenol.

To the resulting slurry which was stirred using a Labline cruciform stainless steel impeller turning at about 6,000 rpm there was added the stirred copper imino acid complex solution prepared above. The resulting mixture was stirred for 15 minutes and heated to 80° C. 1.560 gms of sodium hydroxide (as 39 ml of 1.0 N) solution was added durng the course of the reaction to maintain the pH of the mixture at 9.0. The mixture was stirred under oxygen. The oxygen flow was rapid at the beginning to flush the system. After about ½ hour, oxygen flow was reduced and maintained at a level sufficient to cause slow bubbling in a bubbler attached to the top of the condenser. The temperature was controlled by a Therm-O-Watch. The reaction mixture was stirred vigorously and maintained under oxygen for the prescribed reaction time of 6 hours.

Product Isolation

The reaction slurry was cooled to room temperature, acidified to pH3 with HCl, filtered to remove the water phase, and washed twice with 200 ml with water. A sample of the solid was removed, dissolved in acetone and analyzed by gas-liquid chromatography. The analysis indicated that 99+ weight percent of the 2,6-xylenol was converted.

The solid product was then washed with xylene to remove oligomer and dried at 60° C. overnight. 36.4 gm of product was obtained as a green solid which contained 37.3 weight percent diphenoquinone and 62.7 weight percent tetramethylbiphenol as determined by spectrophotometric analysis.

EXAMPLE 3

Into a first flask there were added:

0.4 grams (2 mmols) of cupric acetate $Cu(OAc)_2 \cdot H_2O$,
0.55 grams (2 mmols) of trisodium nitrolotriacetate
25 grams of ion exchanged water.

Into a 500 ml creased Morton flask, fitted with a gas addition tube, a condenser, a thermometer, and a stirrer capable of operating at speeds in the range of from about 3,000 to about 10,000 rpm there were added; 0.1 grams of sodium lauryl sulfate, 200 grams of deionized water and 48.8 grams (400 mmols) of 2,6-xylenol.

To the resulting slurry which was stirred using a Labline cruciform stainless steel impeller turning at about 6,000 rpm there was added the stirred copper imino acid complex solution prepared above. The resulting mixture was stirred for 15 minutes and heated to 80° C. 1.432 gms of sodium hydroxide (as 35.8 ml of 1.0N) solution was added during the course of the reaction to maintain the pH of the mixture at 9. The mixture was stirred under oxygen. The oxygen flow was rapid at the beginning to flush the system. After about ½ hour, oxygen flow was reduced and maintained at a level sufficient to cause slow bubbling in a bubbler attached to the top of the condenser. The temperature was controlled by a Therm-O-Watch. The reaction mixture was stirred vigorously and maintained under oxygen for the prescribed reaction time of 6 hours.

Product Isolation

The reaction slurry was cooled to room temperature, acidified to pH3 with HCl, filtered to remove the water phase, and washed twice with 200 ml with water. A sample of the solid was removed, dissolved in acetone and analyzed by gas-liquid chromatography. The analysis indicated that 99+ weight percent of the 2,6-xylenol was converted.

The solid product was then washed with xylene to remove oligomer and dried at 60° C. overnight. 43.7 gm of product was obtained as a brown-orange solid which contained 22 weight percent diphenoquinone and 70 weight percent tetramethylbiphenol as determined by spectrophotometric analysis.

EXAMPLE 4

Into a first flask there was added;

0.4 grams (2 mmols) of cupric acetate $Cu(OAc)_2.H_2O$,
1.10 grams (4 mmols) of trisodium nitrilotriacetate
25 grams of ion exchanged water.

Into a 500 ml creased Morton flask, fitted with a gas addition tube, a condenser, a thermometer, and a stirrer capable of operating at speeds in the range of from about 3,000 to about 10,000 rpm there were added; 0.1 grams of sodium lauryl sulfate, 200 grams of deionized water and 48.8 grams (400 mmols) of 2,6-xylenol.

To the resulting slurry which was stirred using a Labline cruciform stainless steel impeller turning at about 6,000 rpm there was added the stirred copper imino acid complex solution prepared above. The resulting mixture was stirred for 15 minutes and heated to 80° C. 4.16 gms of sodium hydroxide (as 104 ml of 1.0 N) solution was added during the course of the reaction to maintain the pH of the mixture at 9. The mixture was stirred under oxygen. The oxygen flow was rapid at the beginning to flush the system. After about ½ hour, oxygen flow was reduced and maintained at a level sufficient to cause slow bubbling in a bubbler attached to the top of the condenser. The temperature was controlled by a Therm-O-Watch. The reaction mixture was stirred vigorously and maintained under oxygen for the prescribed reaction time of 6 hours.

Product Isolation

The reaction slurry was cooled to room temperature, acidified to pH5 with HCl, filtered to remove the water phase, and washed twice with 200 ml with water. A sample of the solid was removed, dissolved in acetone and analyzed by gas-liquid chromatography. The analysis indicated that 99+ weight percent of the 2,6-xylenol was converted.

The solid product was then washed with xylene to remove oligomer and dried at 60° C. overnight. 30.5 gm of product was obtained as a green solid which contained 6.6 weight percent of diphenoquinone and 93.4 weight percent tetramethylbiphenol as determined by spectrophotometric analysis.

EXAMPLE 5

Into a first flask there was added:

0.4 grams (2 mmols) of cupric acetate $Cu(OAc)_2.H_2O$,
36 grams (2 mmols) of N-2-hydroxyethyl iminodiacetic acid,
25 grams of ion exchanged water.

Into a 500 ml creased Morton flask, fitted with a gas addition tube, a condenser, a thermometer, and a stirrer capable of operating at speeds in the range of from about 3,000 to about 10,000 rpm there were added; 0.1 grams of sodium lauryl sulfate, 200 grams of deionized water and 48.8 grams (400 mmols) of 2,6-xylenol.

To the resulting slurry which was stirred using a Labline cruciform stainless steel impeller turning at about 6,000 rpm there was added the stirred copper imino acid complex solution prepared above. The resulting mixture was stirred for 15 minutes and heated to 80° C. 1.520 gms of sodium hydroxide (as 38 ml of 1.0 N) solution was added during the course of the reaction to maintain the pH of the mixture at 9. The mixture was stirred under oxygen. The oxygen flow was rapid at the beginning to flush the system. After about ½ hour, oxygen flow was reduced and maintained at a level sufficient to cause slow bubbling in a bubbler attached to the top of the condenser. The temperature was controlled by a Therm-O-Watch. The reaction mixture was stirred vigorously and maintained under oxygen for the prescribed reaction time of 6 hours.

Product Isolation

The reaction slurry was cooled to room temperature, acidified to pH3 with HCl, filtered to remove the water phase, and washed twice with 200 ml with water. A sample of the solid was removed, dissolved in acetone and analyzed by gas-liquid chromatography. The analysis indicated that 99+ weight percent of the 2,6-xylenol was converted.

The solid product was then washed with xylene to remove oligomer and dried at 60° C. overnight. 35.8 gm of product was obtained as a dark green solid which contained 49.7 weight percent diphenoquinone and 50.3 weight percent tetramethylbiphenol as determined by spectrophotometric analysis.

EXAMPLE 6

Into a first flask there were added;

0.4 grams (2 mmols) of cupric acetate $Cu(OAc)_2.H_2O$,
0.24 grams (1 mmols) of nitrilotripropionic acid,
25 grams of ion exchanged water.

Into a 500 ml creased Morton flask, fitted with a gas addition tube, a condenser, a thermometer, and a stirrer capable of operating at speeds in the range of from about 3,000 to about 10,000 rpm there were added 200 grams of deionized water and 48.8 grams (400 mmols) of 2,6-xylenol.

To the resulting slurry which was stirred using a Labline cruciform stainless steel impeller turning at about 6,000 rpm there was added the stirred copper imino acid complex solution prepared above. The resulting mixture was stirred for 15 minutes and heated to 80° C. 0.640 gms of sodium hydroxide (as 16 ml of 1.0 N) solution was added during the course of the reaction to maintain the pH of the mixture at 9. The mixture was stirred under oxygen. The oxygen flow was rapid at the beginning to flush the system. After about ½ hour, oxygen flow was reduced and maintained at a level sufficient to cause slow bubbling in a bubbler attached to the top of the condenser. The temperature was controlled by a Therm-O-Watch. The reaction mixture was stirred vigorously and maintained under oxygen for the prescribed reaction time of 6 hours.

Product Isolation

The reaction slurry was cooled to room temperature, acidified to pH3 with HCl. filtered to remove the water phase, and washed twice with 200 ml water. A sample of the solid was removed, dissolved in acetone and analyzed by gas-liquid chromatography. The analysis indicated that 94.7 weight percent of the 2,6-xylenol was converted.

The solid product was then washed with xylene to remove oligomer and dried at 60° C. overnight. 30.3 gm of product was obtained as a yellow solid which contained .66 weight percent diphenoquinone and 99. percent tetramethylbiphenol as determined by spectrophotometric analysis.

EXAMPLE 7

Into a first flask there were added;

0.4 grams (2 mmols) of cupric acetate $Cu(OAc)_2 \cdot H_2O$,
0.54 grams (2 mmols) of p-n-butylanilinediacetic acid
25 grams of ion exchanged water.

Into a 500 ml creased Morton flask, fitted with a gas addition tube, a condenser, a thermometer, and a stirrer capable of operating at speeds in the range of from about 3,000 to about 10,000 rpm there were added; 0.1 grams of sodium lauryl sulfate, 200 grams of deionized water and 48.8 grams (400 mmols) of 2,6-xylenol.

To the resulting slurry which was stirred using a Labline cruciform stainless steel impeller turning at about 6,000 rpm there was added the stirred copper imino complex solution prepared above. The resulting mixture was stirred for 15 minutes and heated to 80° C. 1.440 gms of sodium hydroxide (as 36 ml of 1.0 N) solution was added during the course of the reaction to maintain the pH of the mixture at 9. The mixture was stirred under oxygen. The oxygen flow was rapid at the beginning to flush the system. After about ½ hour, oxygen flow was reduced and maintained at a level sufficient to cause slow bubbling in a bubbler attached to the top of the condenser. The temperature was controlled by a Therm-O-Watch. The reaction mixture was stirred vigorously and maintained under oxygen for the prescribed reaction time of 6 hours.

Product Isolation

The reaction slurry was cooled to room temperature, acidified to pH3 with HCl, filtered to remove the water phase, and washed twice with 200 ml with water. A sample of the solid was removed, dissolved in acetone and analyzed by gas-liquid chromatography. The analysis indicated that 99+ weight percent of the 2,6-xylenol was unreacted.

The solid product was then washed with xylene to remove oligomer and dried at 60° C. overnight. 36.8 gm of product was obtained as a dark green solid which contained 31 weight percent diphenoquinone and 69 weight percent tetramethylbiphenol as determined by spectrophotometric analysis.

When the examples are repeated according to the procedure of Example 1 but with the exception that the source of metal ion is changed from divalent copper to either of divalent nickel, cobalt or manganese or trivalent cerium, chromium or ion, similarly satisfactory results are obtained.

In a similar manner when the starting phenol is changed from 2,6-xylenol to 2,6-di-t-butylphenol, 2,6-di-sec-butylphenol, 2-methyl-6-t-butylphenol, 2,6-dimethoxyphenol, 1-naphthol or 2-t-butyl-4-methylphenol while following the procedure of Example 1, satisfactory amounts of c-c coupled products are obtained.

What is claimed is:

1. A method of preparing by an oxidation coupling reaction a carbon-carbon coupled condensation product of an alkyl phenol, an alkoxy phenol, or a 1-naphthol having one of the following formulas:

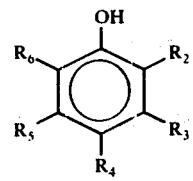

wherein $R_2$ and $R_6$ are alkyl, $R_3$ and $R_5$ are hydrogen or alkyl, and $R_4$ is hydrogen or methyl with the proviso that $R_3$ and $R_5$ cannot both be tertiary alkyl,

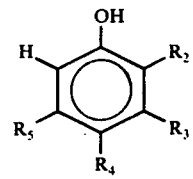

wherein $R_2$ and $R_4$ are alkyl provided that at least one of said alkyl groups is a tertiary alkyl and $R_3$ and $R_5$ are hydrogen or alkyl,

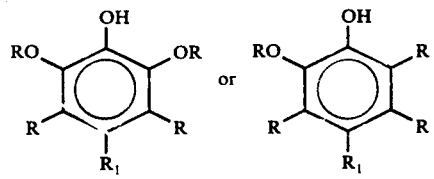

wherein each R is any alkyl group as defined above for the alkylphenols or OR, OR being alkoxy of 1–6 carbon atoms, and $R_1$ is either hydrogen or methyl, provided that the substituents adjacent to $R_1$ cannot both be tertiary alkyl or tertiary alkoxy,

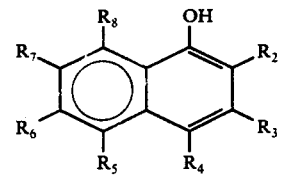

wherein $R_2$, $R_3$ and $R_4$ are hydrogen, alkyl containing from 1 to 5 carbon atoms, or alkoxy containing from 1 to 6 carbon atoms, provided that either or both $R_2$ and $R_4$ are hydrogen and $R_5$, $R_6$, $R_7$, and $R_8$ are hydrogen, alkyl containing from 1 to 5 carbon atoms or alkoxy containing from 1 to 6 carbon atoms provided that tertiary alkyl or tertiary alkoxy groups may not be attached to adjacent carbon atoms of the naphthalene molecule,

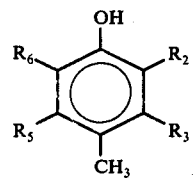

wherein $R_3$ is hydrogen, a primary, secondary or tertiary alkyl or an alkoxy group, $R_5$ is a primary or secondary alkyl group containing from 1–5 carbon atoms and $R_2$ and $R_6$ are a primary, secondary or tertiary alkyl or an alkoxy group, said method comprising contacting an aqueous mixture of the phenol or naphthol with oxygen or oxygen containing gas in the presence of a catalyst system consisting essentially of an imino acetic acid metal complex wherein the metal source is selected from the class consisting of divalent copper, divalent nickel, divalent cobalt, divalent manganese, trivalent cerium, trivalent chromium, and trivalent iron and wherein the imino acid has the formula $$R-N[(CH_2)_nCO_2H]_2$$

wherein $n$ is 1 or 2 and R is hydrogen, alkyl, oxaalkyl, hydroxyalkyl, cycloalkyl, aryl, pyridyl or $-(CH_2)_nCO_2H$ wherein $n$ is 1 or 2 and a sufficient amount of an alkaline material selected from the group consisting of alkali metal hydroxides, alkali metal carbonates and alkali metal bicarbonates to maintain the pH in the range of about 8.5–9.5 during the oxidative coupling reaction.

2. A method, as claimed in claim 1, wherein the aqueous phenol mixture additionally comprises a surfactant.

3. A method, as claimed in claim 1, wherein the surfactant is sodium lauryl sulfate and is present in an amount equal to at least 0.1 mmol per 400 mmols of phenol or naphthol.

4. A method, as claimed in claim 1, wherein the phenol is an alkylphenol.

5. A method, as claimed in claim 1, wherein the alkylphenol is a 2,6-dialkylphenol.

6. A method, as claimed in claim 1, wherein the alkylphenol is 2,6-xylenol.

7. A method, as claimed in claim 1, wherein the catalyst system comprises a cupric iminoacetic acid complex.

8. A method, as claimed in claim 1, wherein the amount of metal complex is equal to at least about 0.2 mmols per mol of phenol or naphthol.

9. A method as claimed in claim 1, wherein the imino acid has the formula $HN(CH_2CO_2H)_2$.

10. A method, as claimed in claim 1, wherein the imino acid has the formula $N(CH_2CO_2H)_3$.

11. A method, as claimed in claim 1, wherein the imino acid has the formula $HOCH_2CH_2N(CH_2CO_2H)_2$.

12. A method, as claimed in claim 1, wherein the imino acid has the formula $N(CH_2CH_2CO_2H)_3$.

* * * * *